United States Patent [19]

Fox, Jr.

[11] Patent Number: 4,559,223
[45] Date of Patent: Dec. 17, 1985

[54] SILVER SULFADIAZINE AND/OR ZINC SULFADIAZINE-CONTAINING TOOTHPASTE OR ORAL MEDICAMENT

[75] Inventor: Charles L. Fox, Jr., New York, N.Y.

[73] Assignee: Daltex Medical Sciences, Inc., New York, N.Y.

[21] Appl. No.: 677,905

[22] Filed: Dec. 6, 1984

Related U.S. Application Data

[63] Continuation of Ser. No. 495,734, May 20, 1983, abandoned, which is a continuation of Ser. No. 272,734, Jun. 11, 1981, abandoned, which is a continuation of Ser. No. 132,207, Mar. 12, 1980, abandoned.

[51] Int. Cl.$^4$ .......................... A61K 7/16; A61K 9/68; A61K 31/18; A61K 31/315
[52] U.S. Cl. ........................................ 424/48; 424/49; 514/157
[58] Field of Search .................... 424/48–58, 424/132, 145, 288, 290, 228

[56] References Cited

U.S. PATENT DOCUMENTS

| 2,422,688 | 6/1947 | Lott | 424/228 |
| 3,761,590 | 9/1973 | Fox | 424/228 |
| 3,792,161 | 2/1974 | Fox | 424/228 |
| 4,020,150 | 4/1977 | Wysor | 424/1 |
| 4,049,802 | 9/1977 | Fox | 424/228 |
| 4,078,058 | 3/1978 | Fox | 424/228 |
| 4,082,841 | 4/1978 | Pader | 424/50 |
| 4,152,418 | 5/1979 | Pader | 424/50 |
| 4,156,716 | 5/1979 | Wagenknecht et al. | 424/48 |
| 4,157,385 | 6/1979 | Wagenknecht et al. | 424/48 |
| 4,157,386 | 6/1979 | La Rochelle | 424/52 |
| 4,160,820 | 7/1979 | Wagenknecht et al. | 424/48 |
| 4,160,821 | 7/1979 | Sipos | |
| 4,160,822 | 7/1979 | Hashimoto et al. | 424/52 |
| 4,164,572 | 8/1979 | Oystese | 424/177 |

FOREIGN PATENT DOCUMENTS 2811522 4/1979 Fed. Rep. of Germany .

Primary Examiner—Shep K. Rose
Attorney, Agent, or Firm—Cooper, Dunham, Clark, Griffin & Moran

[57] ABSTRACT

This invention discloses compositions useful as dentifrices or oral medicaments and capable of inhibiting microbial mouth infections. The compositions contain an effective amount of silver and/or zinc sulfadiazine and a suitable carrier. By inhibiting microbial mouth infections, these compositions reduce or eliminate dental caries, plaque formation, gingival destruction, bone and tooth loss. The compositions of this invention may be in the form of liquids such as mouthwashes, pastes such as toothpastes or solids such as chewing gums or coated dental tapes or flosses.

6 Claims, No Drawings

SILVER SULFADIAZINE AND/OR ZINC SULFADIAZINE-CONTAINING TOOTHPASTE OR ORAL MEDICAMENT

This is a continuation of application Ser. No. 495,734, filed May 20, 1983, which is a continuation of Ser. No. 272,734, filed June 11, 1981, which is a continuation of Ser. No. 132,207, filed Mar. 12, 1980, all now abandoned.

BACKGROUND OF THE INVENTION

Microbial infections in the mouth are known to play a major role in dental caries, plaque formation, gingival destruction and dental erosion with ultimate involvement of bone and loss of teeth.

Dental caries, that is, damage to the tooth surface or enamel is believed to be primarily caused by the formation of dental plaque on and around teeth. The dental plaque, a product of microbial growth, is a dense microbial layer consisting of a mass of microorganisms embedded in a matrix and accumulating on the teeth and in adjacent surfaces. A wide variety of microorganisms are found in the oral cavity, of which some, particularly certain bacteria such as *Streptococcus mutans* can produce acids or other toxic substances, which can cause decomposition of tooth enamel. In addition to microorganisms, dental plaque is composed of numerous other substances such as milk, protein, minerals derived from saliva, dead cells, and food residues which may be dissolved or present in particulate form.

Recent dental research suggests that the major potential for harm by dental plaque resides in the bacteria component thereof. Specifically, bacterial metabolism may result in the production of acids, toxins, and enzymes which are deleterious to neighboring oral tissues. Of particular concern is the production of acid which results in a decline in the pH value of the saliva below its normal pH value of 7.0 to 7.5. The amount of the pH decline of the saliva depends upon the kind, quantity and frequency of food intake. Similar factors also effect the regeneration time, that is, the time required to reattain normal pH value for the saliva. Depending upon the type of food, the pH value of the saliva, and therefore, that on tooth surfaces can drop to pH values 5.5 to 4.5, and in some situations, for example after ingestion of candies or other sweets, even lower pH values may prevail. pH values below 5.5 are generally considered undesirable because such strongly acidic conditions can bring about the result that the calcium compounds of the teeth are dissolved in the saliva. This in turn may lead to damage to the enamel, and eventually to dental caries. It may therefore be concluded that the greater the decline in the pH value on the tooth surface, the more time will be needed for regeneration of normal pH values and the greater the danger of dental corrosion and caries.

Furthermore, the thicker the film or plaque on tooth surfaces, the greater the danger of plaques on the tooth surfaces, acids produced through bacterial metabolism will require considerably more time to reach the surface of the film or plaque and antimicrobial agents require more time to effect bacterial decomposition so that there occur greater variations in the pH value on the tooth surfaces and in regeneration times.

Another problem which is nearly as important as the treatment and prevention of dental caries is the treatment and prevention of periodontitis at the stage of inflammation of the gingivae. An important aspect of the treatment of periodontitis is the reduction of tartar deposits deep in the pouches, which are associated with the loosening of the teeth symptomatic of this condition.

It has previously been disclosed that silver sulfadiazine possesses antibacterial properties and that silver sulfadiazine is useful in the topical treatment of burns. See for example, U.S. Pat. No. 3,761,590. It has also been previously disclosed that zinc sulfadiazine possesses antibacterial properties and is useful in burn therapy. See, for example, U.S. Pat. No. 4,049,802. Also there have been prior art disclosures of the use of zinc containing compounds or compositions in connection with dental care, including the reduction of dental plaque and dental caries. See, for example, U.S. Pat. No. 4,146,607, 4,082,841 and 4,152,418.

In accordance with the present invention it has been unexpectedly established that both the formation of dental plaque on the surfaces of teeth which is associated with dental caries and gingivitis or periodontitis can be eliminated or at least reduced to a substantial extent if silver and/or zinc sulfadiazine are added to a regularly used tooth or mouth caring composition such as a toothpaste, mouthwash, dental chewing gum or dental floss or tape.

SUMMARY OF THE INVENTION

The present invention provides compositions useful as dentirifices or oral medicaments which are capable of inhibiting microbial mouth infections and which contain an effective amount of silver and/or zinc sulfadiazine and a suitable carrier. By virtue of their property of inhibiting microbial mouth infections, the compositions of this invention are useful in reducing or eliminating dental caries, plaque formation and gingivitis. The compositions of this invention include toothpastes, mouthwashes, dental chewing gums and dental tapes or flosses.

DETAILED DESCRIPTION OF THE INVENTION

This invention provides compositions wherein zinc and/or silver sulfadiazine are incorporated in effective amounts into pastes or powders for use on toothbrushes; into mixtures with cement for topical application by dentists; into suspensions or effervescent tablets for use in mouthwashes; into chewing gums including those which may be formulated so as to release active ingredients gradually thereby prolonging their duration of contact with the surfaces of teeth and gums; and, finally, into dental tapes or flosses used to clean teeth mechanically.

The utility of the compositions of this invention is based not only on the antimicrobial activity of the compounds zinc sulfadiazine and silver sulfadiazine, but also, particularly in the case of zinc sulfadiazine, on the propensity of the zinc to bind to the hydroxyapatite which is the principal component of the enamel and dentin of the teeth. Suppression of microbial growth reduces acid production by inhibiting glycolysis. As a result the reduced pH on the surfaces of teeth which is associated with dental caries is reduced or eliminated.

One obvious advantage of the compounds silver and zinc sulfadiazine is the fact that while the metals silver and zinc are known to inhibit microbial growth, these metals have previously been used in dental fillings to replace tooth loss from decay. In addition, these compounds contain the sulfonamide moiety which has been shown to be active in suppressing microbial growth. The combination, i.e. silver sulfadiazine or zinc sulfadiazine, results in minimally soluble substances of low toxicity which provide the advantage of controlling microbial growth over long spans of time. Zinc sulfadiazine is particularly useful in that it facilitates incorporation of zinc into certain tooth components.

The compositions of the present invention containing silver and/or zinc sulfadiazine are believed to function by virtue of their wide-ranging antimicrobial action so that they reduce or destroy both those bacteria responsible for periodontitis and those bacteria which are associated with dental plaque and caries. The compositions through their antimicrobial properties are believed to reduce or eliminate the undesirable pH declines on tooth surfaces described hereinabove. The effects of silver and/or zinc sulfadiazine may be supplemented by the use of additional materials particularly those which are commonly used to inhibit dental caries and periodontitis such as fluoride ion-containing materials.

In accordance with this invention, useful preparations may be prepared which contain effective amounts of silver and/or silver sulfadiazine, that is, amounts from about 0.5 to about 10.0 percent by weight. The balance of the compositions in accordance with this invention consists of a suitable carrier or carriers and other substance which may be desirably included in minor amounts. For example, where the preparation contemplated is a mouthwash, the balance of the preparation will consist essentially of water or water and a mono- or polyhydric alcohol such as ethanol, glycerol, or sorbitol, and optionally, flavoring substances and foaming agents. If glycerine or sorbitol are present they will serve to sweeten the preparation.

Surfactants or suspending agents are usually present in mouthwashes as solubilizers for essential flavoring oils. The customary solubilizers for this purpose are the sorbitan fatty acid esters, the polyoxyethylene derivatives thereof and polyoxyethylene fatty acid ethers. In addition, the mouthwash formulation may contain one or more of the well-known, highly active antibacterial agents, such as neomycin sulfate, hexachlorophene, halogenated salicylanilides, compatible quaternary ammonium compounds and the like. Depending upon the particular carrier or carriers employed, the zinc and/or silver sulfadiazine may be dissolved or suspended in the mouthwash formulation.

When the composition is a toothpaste, there may be additionally present polishing agents, flavoring substances, sweetening substances, foaming agents and the like. It will be understood that the polishing agents and other components suitable for use in the toothpastes of this invention must be compatible with the zinc and/or silver sulfadiazine.

Among the suitable inorganic polishing agents useful in accordance with the present invention are silica xerogels and silica aerogels. The xerogels are synthetic, aggregated, amorphous, highly porous silicas having generally a mean particle diameters of about 4 to 10 microns. The aerogels have mean particle diameters of about 3 to 12 microns and are somewhat more porous than the xerogels. Other polishing agents are known in the art and may be used in addition to or instead of the aforementioned xerogels and aerogels.

The polishing agent should be in the form of fine particles as is well known in the art. Preferably, the particles should be of such size that at least 40% pass through a 325 mesh screen and at least 90% pass through a 20 mesh screen. The finer particles within this size range are preferred, particularly a size distribution such that all particles pass through a 20 mesh screen, more than 90% pass through a 100 mesh screen, more than 80% pass through a 200 mesh screen, and more than 40% pass through a 325 mesh screen. Especially preferred are the finer particles having a mean particle diameter of about 3 to about 44 microns.

In toothpaste formulations it is preferable that the zinc and/or silver sulfadiazine be present in the form of finely pulverized particles having a particle size less than about 5 microns, preferable a particle size in the range from about 0.5 to about 3.0 microns.

Polymer particles of various types are useful as abrasives in the toothpaste compositions of the present invention. A particularly useful polymer is polyethylene in powder form of such size that more than 40% passes through a 325 mesh screen, more than 80% passes through a 200 mesh screen, at least 85% passes through a 100 mesh screen, and 90 to 100% passes through a 20 mesh screen. Other substances proposed as dental abrasives include various abrasive materials such as silica imbedded in protective plastic particles.

Polishing agents may be present in the toothpastes of this invention over the broad range of about 1 to 70%, preferably 10% to 60%, and typically from about 20% to 50%. In a tooth powder the polishing agent will be present in somewhat higher amount such as amounts in the range from about 50 to 99%, preferably about 70% to 95%, and typically from about 90% to about 95%.

The toothpastes will usually also contain compatible bodying agents such as gum Tragacanth, starch, sodium carboxymethylcellulose, Irish moss, gum arabic, sodium carboxymethylhydroxyethylcellulose, and the like. When present, these will usually be at levels of from about 0.5% to about 3%, preferably from about 0.8% to about 1.5%.

Humectants are also desirable in a toothpaste. These will usually be compounds as glucose, honey, glycerol, propylene glycol, sorbitol, polyethylene glycol 400, and other polyhydric alcohols, and may be present in amounts up to about 80% by weight.

Other adjuvants may also be present, such as fluorine compounds, chlorophyll compounds, flavor substances, saccharin, urea, ammonium compounds, alcohol, mineral oil, foaming agents or detergents, such as sodium lauryl sulfate, dodecanesulfonate, acyl taurines, acyl isethionates, etc., depending upon the form of the product.

During experiments conducted with mouth caring compositions which contained silver sulfadiazine, the following results were obtained.

In the case of bacterial infections of the oral cavity and, in particular, of the gingival edges, a considerable reduction of pathogenic bacteria was noted and as a consequence of this reduction, healing was achieved within a short time when a toothpaste containing in addition to conventional ingredients 2% silver sulfadiazine was applied four times daily for a period of about 3 minutes each application.

With the addition of 1% silver sulfadiazine to a toothpaste of an otherwise conventional composition, the twice daily application of the paste for prophylaxis results in considerable reduction of the bacterial count in the oral area. A parallel double-blind study with the application of a paste of the same composition, excluding the silver sulfadiazine, demonstrated no change in the bacterial count in the oral area.

When applying 1.5% silver sulfadiazine-containing toothpaste with an otherwise commercially available composition over a long period of time, one could observe a prophylactic effect in respect to gingival bleeding, caries, and peridontitis due to bacterial reduction as observed at semi-annual follow-up examinations.

In the case of bacterial infections of the oral area, in particular inflammations of the gingival and periodontis, one could note healing after about one week, if toothpaste containing 3% silver sulfadiazine and other conventional ingredients was used four times daily.

Upon treating teeth with a liquid dispersion containing 1% zinc sulfadiazine using an oral douche a prophylactic effect against bacterial infections in the oral area was observed.

The most favorable results was observed when the silver and/or zinc sulfadiazine was applied in the form of particularly fine particles, that is, particles smaller than about 5 microns, preferably from about 0.5 to about 3 microns. It is believed that the results observed were obtained because this particle size permitted especially good penetration of the silver and/or zinc sulfadiazine into the lower layers of the tooth and under the inflamed parts of the gingival edge.

The present invention may be further understood by reference to the following examples which are set forth to illustrate the practices of this invention but are not intended in any way to limit the scope thereof.

EXAMPLE 1

Freshly extracted teeth were rinsed several times with saline and each tooth was suspended in 5 ml nutrient broth containing different concentrations of silver sulfadiazine and zinc sulfadiazine. One tooth was suspended in nutrient broth alone and served as the control. The tubes containing the teeth were incubated at 37° C. for 24-48 hours and bacterial growth observed. From Table I it can be seen that even in the tube containing the lowest concentration (0.006 $\mu$mole/ml) of silver sulfadiazine and zinc sulfadiazine, there was no bacterial growth whereas the control tube had dense growth.

TABLE I

In Vitro Effect of Silver Sulfadiazine and Zinc Sulfadiazine on the Growth of Oral Bacteria

| Drugs | (Concentration of Drug) $\mu$mole/ml | | | | | |
|---|---|---|---|---|---|---|
|  | 0.1 | 0.05 | 0.025 | 0.0125 | 0.006 | 0 |
| AgSD | − | − | − | − | − | + |
| ZnSD | − | − | − | − | − | + |

EXAMPLE 2

10 ml thioglycollate medium containing various amounts of silver sulfadiazine or zinc sulfadiazine was inoculated with 0.1 ml of $10^{-2}$ dilution of 48 hour old culture of *Strept. mutans*. The tubes were incubated at 37° C. and the bacterial growth evaluated after 24 and 48 hours. In these studies the lowest concentration employed was 0.0125 $\mu$mole/ml. Both silver sulfadiazine and zinc sulfadiazine are active at this concentration in inhibiting the growth of *Strept. mutans* as shown in Table II.

TABLE II

Effect of AgSD and ZnSD on the In Vitro Growth of strept. Mutans 6715*

|  | (Concentration of Drug) $\mu$mole/ml | | | | |
|---|---|---|---|---|---|
|  | 0.1 | 0.5 | 0.025 | 0.0125 | 0 |
| AgSD | − | − | − | − | + |
| ZnSD | − | − | − | − | + |

*The drug was added in desired concentration in thioglycollate medium and was inoculated with $10^{-2}$ dilution of 48 hour old culture of strept. Mutans and incubated for 48 hours.

EXAMPLE 3

Freshly extracted human teeth were collected in tap water and scalded to remove deposits. They were autoclaved in test tubes for 15 minutes at 120° C. After sterilization the teeth were immersed in 2 ml of 10 $\mu$mole/ml suspensions of silver sulfadiazine or zinc sulfadiazine for 2 minutes. They were taken out and air dried for 1 minute and washed with 200 ml distilled water. These treated teeth were suspended in 10 ml of thioglycollate medium and inoculated with 0.1 ml of $10^{-2}$ dilution of 48 hour old *Strept. mutans* culture. The tube containing the tooth processed as above without the drug treatment served as the control.

Two minutes treatment of the teeth in a 10 $\mu$mole/ml suspension of either silver sulfadiazine or zinc sulfadiazine prevented plaque formation in the presence of *Strept. mutans*.

EXAMPLE 4

Freshly extracted teeth were rinsed several times with water and suspended in 2 ml of $^{110}$silver sulfadiazine or $^{65}$zinc sulfadiazine (5 $\mu$mole/ml). At desired intervals the teeth were removed, washed several times and the radioactivity measured, and then the teeth were resuspended in the same solution.

In the case of silver sulfadiazine a maximum uptake of 1.2 $\mu$mole/ml is attained within 4 hours of contact with the teeth. Uptake of zinc is seen to be higher than the silver and the maximum uptake is obtained after 24 hours, as shown in Table III.

TABLE III

Uptake of Silver Sulfadiazine and Zinc Sulfadiazine by Human Teeth

| Drug | Uptake in $\mu$moles per gram tooth Hours | | |
|---|---|---|---|
|  | 3½ | 6 | 24 |
| AgSD | 1.2 | 1.0 | 1.0 |
| ZnSD | 1.0 | 1.1 | 1.9 |

EXAMPLE 5

Mice were gavaged with aqueous suspension of AgSD or ZnSD (volume not exceeding 0.5 ml) in desired amounts and observed for 2-3 days.

In mice the $LD_{50}$ of AgSD is above 800 mg/kg body wt and that of ZnSD is above 1000 mg/kg.

TABLE IV

Oral Toxicity of AgSD and ZnSD in Mice

|  | Dose (mg/kg) | Died/total |
|---|---|---|
| AgSD | 200 | 0/4 |
|  | 400 | 0/4 |
|  | 600 | 0/4 |
|  | 800 | 0/4 |
| ZnSD | 200 | 0/4 |

TABLE IV-continued
Oral Toxicity of AgSD and ZnSD in Mice

| Dose (mg/kg) | Died/total |
|---|---|
| 400 | 0/4 |
| 600 | 0/4 |
| 800 | 0/4 |
| 1000 | 0/4 |

EXAMPLE 6

A toothpaste was prepared containing the following ingredients:

| by weight | |
|---|---|
| 20.0% | glycerin |
| 2.5% | saccharin |
| 1.2% | carboxymethylcellulose |
| 31.0% | calcium carbonate |
| 1.0% | silver sulfadiazine |
| 2.0% | silica dioxide |
| 2.5% | fatty alcohol sulfate |
| 38.6% | water |
| 0.2% | methanol |
| 1.0% | aromatic oil |

EXAMPLE 7

A toothpaste was prepared containing the following:

| by weight | |
|---|---|
| 20.0% | glycerin |
| 1.0% | carboxymethylcellulose |
| 28.5% | calcium carbonate |
| 1.0% | silver sulfadiazine |
| 0.5% | zinc sulfadiazine |
| 1.0% | fatty alcohol sulfate |
| 3.5% | silica dioxide |
| 38.5% | water |
| 1.0% | aromatic oil |

EXAMPLE 8

A toothpaste was prepared containing the following:

| by weight | |
|---|---|
| 10.0% | glycerin |
| 5.0% | saccharin |
| 1.0% | carboxymethylcellulose |
| 25.0% | calcium carbonate |
| 3.0% | silver sulfadiazine |
| 1.0% | fatty alcohol sulfate |
| 3.0% | silica dioxide |
| 3.0% | paraffin oil |
| 48.0% | water |
| 1.0% | flavoring additive |

EXAMPLE 9

A toothpaste was prepared containing the following:

| by weight | |
|---|---|
| 30.0% | glycerin |
| 2.5% | saccharin |
| 1.0% | carboxymthylcellulose |
| 30.5% | calcium phosphate |
| 7.0% | zinc sulfadiazine |
| 2.0% | fatty alcohol sulfate |
| 2.5% | silica alcohol sulfate |
| 23.3% | water |
| 0.2% | methanol |
| 0.5% | oil of wintergreen |
| 0.5% | flavoring additive |

EXAMPLE 10

A toothpaste was prepared containing the following:

| by weight | |
|---|---|
| 30.0% | glycerin |
| 2.5% | saccharin |
| 1.0% | carboxymethylcellulose |
| 36.5% | dicalcium phosphate |
| 1.0% | silver sulfadiazine |
| 2.0% | fatty alcohol sulfate |
| 26.0% | water |
| 1.0% | flavoring additive |

EXAMPLE 11

A tooth powder was prepared containing the following:

| by weight | |
|---|---|
| 2.0% | silver sulfadiazine |
| 0.5% | silica dioxide |
| 0.01% | sodium saccharide |
| 0.5% | calcium cyclamate |
| 6.55% | aluminum hydroxide |
| 40.0% | tricalciumphosphate |
| 50.0% | aluminum hydroxide |

EXAMPLE 12

The following toothpaste formulation containing zinc sulfadiazine was prepared:

| parts by weight | |
|---|---|
| 100.0 | Sorbo (70% Sorbitol in water) |
| 4.0 | zinc sulfadiazine |
| 0.6 | sodium saccharine* |
| 7.0 | sodium lauryl sulfate |
| 60.0 | Carbopol 934 dispersion (6% in H$_2$O) |
| 48.4 | water |
| 3.1 | sodium hydroxide (50% in H$_2$O) |
| 180.0 | dibasic calcium phosphate-dihydrate |

*Sodium Saccharine - 530 mg saccharin was mixed with 2.9 mmole of NaOH.

Procedure:

Dissolve 7 gms of sodium lauryl sulfate in 16.3 ml water. Mix Sorbo (77 ml); sodium saccharine (0.6 gms) and 6% carbopol solution (60 ml) with 32.1 ml water. Blend the above 2 solutions carefully to avoid foaming. 4 gm of zinc sulfadiazine made into a paste with water is added to the solutions while the blender running. Following this addition, calcium phosphate (140 gm of anhydrous dibasic calcium phosphate mixed with 40 ml water) is slowly added as the mixing continues. After the mixture becomes uniform NaOH (3.1 ml) is added and mixed well.

As will be obvious to one skilled in the art, many modifications, variations and alterations may be made in the practices of the present invention without departing from the spirit and scope thereof as set forth in the preceding description and the claims which follow.

What is claimed is:

1. A method of inhibiting microbial mouth infections and dental caries, plaque formation, gingival destruction and tooth loss associated therewith, which comprises contacting teeth and adjacent gingival surfaces with a composition comprising a suitable carrier and an effective antimicrobial amount of silver and/or zinc sulfadiazine for an effective period of time greater than about 30 seconds to inhibit microbial growth.

2. A method as in claim 1 wherein said composition is a toothpaste.

3. A method as in claim 1 wherein said composition is a mouthwash.

4. A method as in claim 1 wherein said composition is contained in a chewing gum, polishing agent, or dental floss.

5. A method as in claim 1 wherein said composition is contacted to the teeth and/or adjacent gingival surfaces for a period of time of about 3.0 minutes.

6. A method of inhibiting microbial infections and dental caries, plaque formation, gingival destruction and tooth loss associated therewith which comprises contacting teeth and/or adjacent gingival surfaces with a composition comprising sorbitol, sodium, saccharin, sodium lauryl sulfate, a water-soluble thickening and gel-forming resin, water, dibasic calcium dihydrate and an effective antimicrobial amount of zinc sulfadiazine for an effective period of time greater than about 30 seconds to inhibit microbial growth.

* * * * *